United States Patent
Strandberg (10) Patent No.: US 6,871,097 B1
(45) Date of Patent: Mar. 22, 2005

(54) PACEMAKER USING MEASURED INTERVALS FOR MODE SWITCHING

(75) Inventor: Hans Strandberg, Sundbyberg (SE)

(73) Assignee: St. Jude Medical AB, Järfälla (SE)

( * ) Notice: Subject to any disclaimer, the term of this patent is extended or adjusted under 35 U.S.C. 154(b) by 237 days.

(21) Appl. No.: 10/031,757

(22) PCT Filed: Jun. 19, 2000

(86) PCT No.: PCT/SE00/01307
§ 371 (c)(1),
(2), (4) Date: Jan. 17, 2002

(87) PCT Pub. No.: WO01/05465
PCT Pub. Date: Jan. 25, 2001

(30) Foreign Application Priority Data

Jul. 19, 1999 (SE) .............................................. 9902735

(51) Int. Cl.$^7$ .............................................. A61N 1/365
(52) U.S. Cl. .......................................... 607/25; 607/14
(58) Field of Search ................................ 607/9, 14, 17, 607/25

(56) References Cited

U.S. PATENT DOCUMENTS

| | | | |
|---|---|---|---|
| 5,085,215 A | | 2/1992 | Nappholz et al. .............. 607/17 |
| 5,144,949 A | | 9/1992 | Olson ........................... 607/17 |
| 5,325,856 A | | 7/1994 | Nitzsche et al. ............ 600/516 |
| 5,441,523 A | * | 8/1995 | Nappholz ..................... 607/14 |
| 5,514,164 A | | 5/1996 | Mann et al. ................... 607/25 |
| 5,683,428 A | | 11/1997 | Franberg et al. .............. 607/14 |
| 5,788,717 A | * | 8/1998 | Mann et al. ................... 607/14 |
| 5,792,192 A | | 8/1998 | Lu ............................... 607/14 |
| 5,893,882 A | * | 4/1999 | Peterson et al. .............. 607/14 |
| 6,058,326 A | * | 5/2000 | Hess et al. ...................... 607/9 |

FOREIGN PATENT DOCUMENTS

EP 0 596 319 5/1994 .......... A61N/1/368

* cited by examiner

Primary Examiner—Carl Layno
(74) Attorney, Agent, or Firm—Schiff Hardin LLP (57) ABSTRACT

A pacemaker is operable in a tracking and a non-tracking mode and has an automatic mode switching function for switching the pacemaker into the non-tracking mode of operation in response to the detection of atrial tachycardia. A comparator compares an atrial interval, between detected atrial events, with a predetermined atrial tachycardia limit value and records a tachycardia indication if the interval is less than the atrial tachycardia limit value. The mode switching unit switches the mode of operation to the non-tracking mode if the number of recorded tachycardia indications reaches a predetermined tachycardia count limit. Intervals between other cardiac events detected by the atrial detector or a ventricular detector also are supplied to the comparator wherein they are compared with the atrial tachycardia limit value. The recorded number of tachycardia indications is reduced by one if at least one of these additional intervals, during a pacemaker interval between two consecutive ventricular stimulations or between two consecutive R-wave detections, is longer than the tachycardia limit value.

13 Claims, 8 Drawing Sheets

Pacemaker System Overview

Pacemaker System Overview

PACEMAKER USING MEASURED INTERVALS FOR MODE SWITCHING

BACKGROUND OF THE INVENTION

1. Field of the Invention

The present invention relates to a pacemaker of the type that is operable in a tracking and a non-tracking mode and having an automatic mode switching function for switching the pacemaker into a non-tracking mode of operation in response to the detection of an atrial tachycardia, and including an atrial detector for detecting atrial events, a ventricular detector for detecting ventricular events, an atrial interval determining unit for determining the interval between consecutive atrial events, a comparator for comparing this interval with a predetermined atrial tachycardia limit value for recording a tachy indication if the interval is less than the atrial tachycardia limit value, and a mode switching unit for switching the mode of operation to the non-tracking mode when the number of recorded tachy indications reaches a predetermined tachy count limit.

2. Description of the Prior Art

Patients with paroxysmal atrial tachycardias who require e.g. DDD pacing run the risk of entering into a situation of inappropriate rapid pacing due to tracking of the atrial rhythm. It has been observed that a non-physiologic high ventricular stimulation rate in a tracking mode of operation is the primary source of the suffering of the patient and not the atrial tachycardia in itself. As a rule, more than 50% of patients, which have had periods of atrial tachycardia before the implantation of a pacemaker, will have it again, and more than 30% of pacemaker patients which have not had any suspected atrial tachycardia will get at least one episode of tachycardia during a five year period after implantation. If these patients were paced with a pre-set rate, possibly modulated by a rate-adaptive sensor, they would not have AV synchrony during periods of sinus rhythm and therefore be compromised. Several solutions employing mode switching have therefore been proposed to avoid inappropriate tracking of atrial arrhythmias and to provide tracking of the sinus mode at all other times. Usually such a mode switch of the pacemaker changes the mode of response to atrial sensed events from a tracking to a non-tracking mode. When the atrial rhythm exceeds a predetermined detection rate for a set number of intervals the ventricle will consequently be paced at a predetermined rate and when sinus rhythm resumes, the pacemaker is switched back to an atrial tracking mode.

Thus in U.S. Pat. No. 5,085,215 a metabolic demand driven rate-responsive pacemaker is described, which is switched into a VVI mode, when a maximum atrial tracking rate is reached. In the VVI mode ventricular pacing pulses are generated at a rate which is a function of a metabolic indicator rate and independent of atrial heartbeat sensing.

U.S. Pat. No. 5,514,164 discloses an implantable pacemaker normally operating in a DDD mode and reverting to a modified DDI mode in response to the sensing of atrial depolarization early in the pacing cycle. The DDI mode operates in the same way as the DDD mode except that the atrial signals are not tracked. Hence, detection of P-waves in the DDI mode result in inhibition of atrial output with normal ventricular timing. The DDI mode continues only to the end of the pacing cycle. During the next pacing cycle the DDI mode is initiated again only if a P-wave is again sensed early in the pacing cycle, otherwise DDD pacing continues.

There is a need for improvement of automatic mode switch algorithms known today.

Some known algorithms may be considered slow because of too long a period of confirmation before the mode switch occurs and some systems switch mode incorrectly caused by improper detector design resulting in false indications in conjunction with too short a confirmation period. Some automatic mode switch systems do not have a reliable signal sensing, which may also result in non-detection of some cardiac events. Further, unnecessarily long refractory periods of known systems may give blindness to atrial tachycardia and the time from tachycardia starts until mode switch is very unpredictable and dependent on the tachycardia rate or programmed tachycardia limit.

There does not exist any automatic mode switch design today, which is suitable for all types of patients. A few patients prefer a longer time for the mode switching, typically several seconds, if false mode switchings can be avoided in this way. However, most patients want to avoid any unnecessarily high stimulation rates, even for a few seconds.

A correct signal detection is the first and most important factor for a satisfactory mode switch function. Several types of pacemakers are provided with only one atrial signal detector. When the sensitivity of this detector is adjusted appropriately for detection of normal P-waves, some types of atrial tachycardias will be detected only intermittently. The mode switching then has to be based on "guessings". Further, during pacemaker implantation and the accompanying follow-up atrial tachycardia signals are most often not obtainable. It is therefore an obvious risk that the physician will choose a sensitive setting, which is too high or too low for atrial tachycardia detection. Often a very high sensitivity is chosen, which together with unsuitable filter designs may result in the detection of R-wave farfields and also interferences, which may influence the normal pacing rate and even give rise to false mode switches.

This detector sensitivity dilemma is one reason for a problematic mode switch function of several existing products.

Thus, to distinguish an atrial tachycardia from an interference or some premature heart signals merely by measurement of atrial intervals and counting the number of such intervals might not be sufficient. As a matter of fact several factors have to be considered.

If farfield R-waves are sensed by the atrial detector the pulse generator timers of the pacemaker will be restarted with restart of refractory periods as well. Ventricular stimulations with accompanying blanking periods are also synchronized to the sensed atrial signal, the stimulation rate being of course limited by the maximum tracking rate. The blanking intervals, which may cover atrial events, are consequently repeated more frequently. All these intervals resulting from a mixture of sensed and stimulated events must be considered when designing an automatic mode switch system and not only the free atrial—atrial signals.

If spontaneous ventricular beats are omitted, three different situations of mixed sensed and stimulated cardiac occurrences are possible during an atrial tachycardia in DDD mode of operation of a pacemaker. These situations are illustrated by symbolic ECG's designated a, b and c in FIG. 1 a), b) and c).

Figure 1:
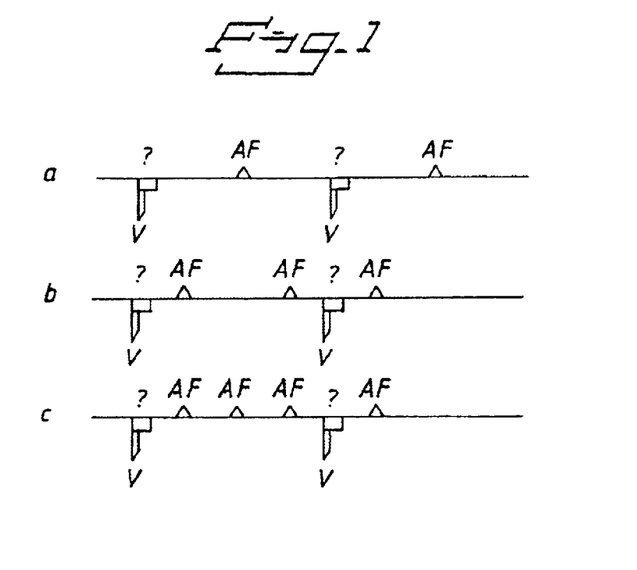
FIG. 1, as noted above, shows symbolic ECG's for three different situations of mixed cardiac events.

AF denotes an atrial signal, which can be a P-wave, flutter or fibrillation sensed on the atrial electrode. V denotes a ventricular stimulation pulse, and ? denotes the associated blind atrial blanking period, during which an atrial signal may have occurred.

The situation illustrated at a) in FIG. 1 is characterized by one atrial signal AF intervening between two ventricular stimulations V. An atrial signal can be hidden during the atrial blanking ?. Since this situation can be stable during an atrial flutter, it can be hard to distinguish between atrial flutter and a normal situation with a high sinus rate without any hidden signals. Even if not all the atrial signals are hidden during an unstable tachycardia, a sufficient number of atrial signals can disappear such that a pacemaker, the control of which is based on long/short atrial intervals, can be wrongly operated. The only effective solution to this problem is to change the stimulation interval, such that when the time of ventricular stimulation is altered, the atrial blanking interval will not be positioned on half the atrial—atrial signal interval.

The situation according to b) in FIG. 1 with two atrial signals AF between two consecutive ventricular stimulations V will make detection possible for all situations provided that the used pulse generator design does not involve unnecessary refractory periods. The algorithms used for controlling the pacemaker can be more or less effective in situations of coverage of some of the atrial signals by the post ventricular atrial blanking periods ?, because there will be a measured long atrial interval which can counteract the tachycardia determination.

At c) in FIG. 1 a situation is shown with three atrial signals AF appearing between each two consecutive ventricular stimulations V. In this case correct AF detection will be possible, provided that the pulse generator design does not involve unnecessary refractory periods and provided that there is no interference protection, which may be erroneously operated by the detected high rate. For this situation, with a very high atrial rate, there is a higher probability for coverage of some of the atrial signals by the post ventricular atrial blanking periods?. If long atrial counting intervals are used in the algorithms for controlling the pacemaker, a slowing down can occur before the mode switch.

Only at extremely high atrial rates and extreme parameter settings four atrial signals AF may occur in one V—V interval. This case is basically similar to the situation shown at c).

Another important factor, which may give rise to problems, is the consideration time from a detection of a short AF—AF interval until a mode switch takes place. Depending on the signal detector design the needed confirmation time will be shorter or longer for one and the same patient depending on the sequence of heart signals in conjunction with other pacemaker timings, such as refractory periods and stimulation intervals. This means that the mode switch confirmation time very often cannot be predicted.

SUMMARY OF THE INVENTION

An object of the present invention is to provide a pacemaker operable in a tracking or a non-tracking mode of operation having an improved mode switching function for switching the pacemaker into the non-tracking mode of operation in response to the detection of an atrial tachycardia.

This object is achieved in the pacemaker according to the present invention, by not only analyzing atrial intervals but also other cardiac event intervals during a predetermined number of stimulation intervals to obtain a safe indication of whether tachycardia exists.

If the atrial—atrial signal interval is shorter than the tachycardia limit value and no other cardiac event interval is longer than this limit in the considered V—V interval, this is used as a tachy indication. If at least one measured interval between any combination of sensed cardiac events or simulations during a V—V interval is longer than the tachycardia limit value this is considered as a non-tachy indication. If there is no atrial indication of tachy nor any indication of non-tachy during an V—V interval, then the mode change counter is not altered.

In the pacemaker according to the invention the necessary logic of the mode switching means is reduced compared to prior art designs. Due to its simplicity it will be more safe and easier to validate. Further, the number of programmable parameters will be few, which consequently reduces the work of the physician and reduces the risks of mistakes. The time from the start of tachycardia to the mode switch and back in the opposite direction is predictable and independent of the tachycardia rate, and can be selected in accordance with the patient's preferences.

In an embodiment of the pacemaker according to the invention the atrial detector is a P-wave detector for detecting ordinary P-waves and an atrial tachycardia detector of higher sensitivity for monitoring atrial tachycardia signals. Thus synchronization and stimulation are controlled by a detector having sensitivity suitable for detection of normal P-waves, while the monitoring for detecting an atrial tachycardia is performed by a more sensitive detector. In this way the above mentioned detector sensitivity dilemma is remedied.

In other embodiments of the pacemaker according to the invention the mode switching unit includes an up/down counter which is incremented by one at each tachy indication and decremented by one at each non-tachy indication. When the number of ventricular stimulation intervals with indicated tachy has reached a programmed limit, a mode switch to the non-tracking mode occurs. The programmed limit preferably is in the range of 1–8 intervals. In this way a higher security is obtained for switching modes only in response to the detection of a true tachycardia. If, on the other hand, longer intervals are detected in the non-tracking mode of operation, a consideration process starts for eventually switching back to the tracking mode. If indications of non-tachycardia are obtained during the consideration process, the counter is counted down and when the counter reaches a predetermined limit the mode switching unit is triggered to change the mode of operation back to the tracking mode. Thus, in the non-tracking mode of the pacemaker, the mode switching unit is adapted to switch mode of operation back to the tracking mode when its tachy indication counter is counted down by a predetermined number from the predetermined tachy count limit.

In another advantageous embodiment of the Pacemaker according to the invention a unit is provided for changing the AV interval in order to uncover possible atrial events covered by the ventricular blanking period. In this way a more reliable detection of the atrial tachycardia is achieved and consequently a more reliable mode switch function.

The stimulation rate can be P-wave controlled, atrial tachycardia signal controlled during the transitional phase of considering a mode switch or equal to a base rate in case of failing heart activity. In an embodiment of the pacemaker according to the invention the base rate is sensor controlled.

DESCRIPTION OF THE PREFERRED EMBODIMENTS

Figure 2:
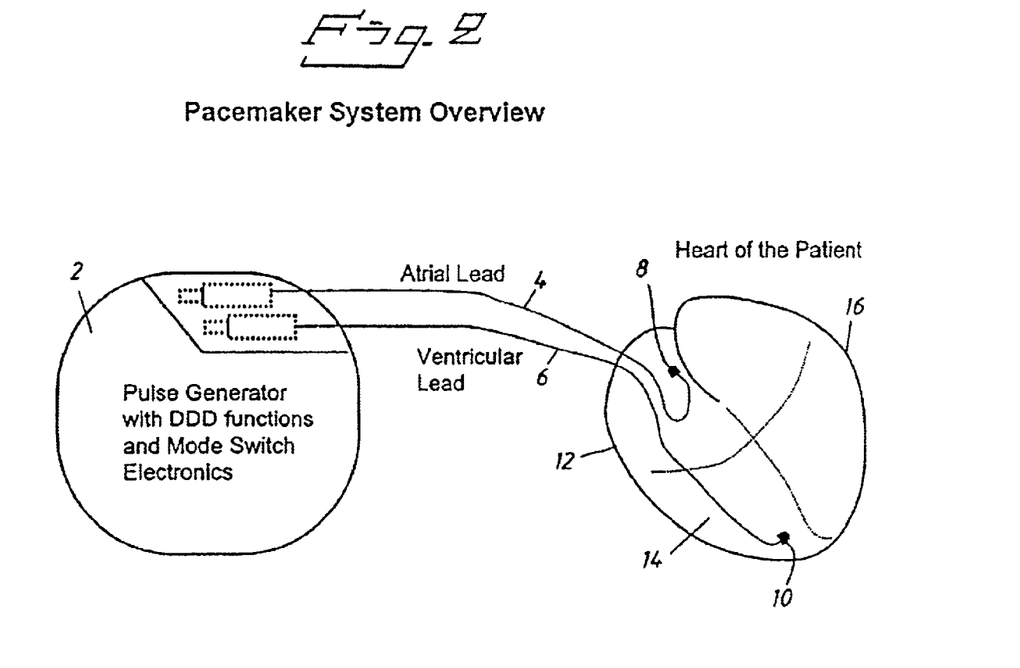
FIG. 2 shows an overview of a pacemaker system according to the invention.

FIG. 2 shows an overview of the whole system of the pacemaker according to the invention including a pulse generator 2 with DDD functions and mode switch electronics for changing the mode of operation from the tracking DDD mode to a non-tracking mode of operation, like a DDI mode, in response to the detection of an atrial tachycardia, and back again to the tracking DDD mode when the tachycardia no longer is detected. The pacemaker 2 is connected through atrial and ventricular leads 4, 6 including associated electrodes 8, 10 to the atrium 12 and the ventricle 14 respectively of a patient's heart 16.

Figure 3:
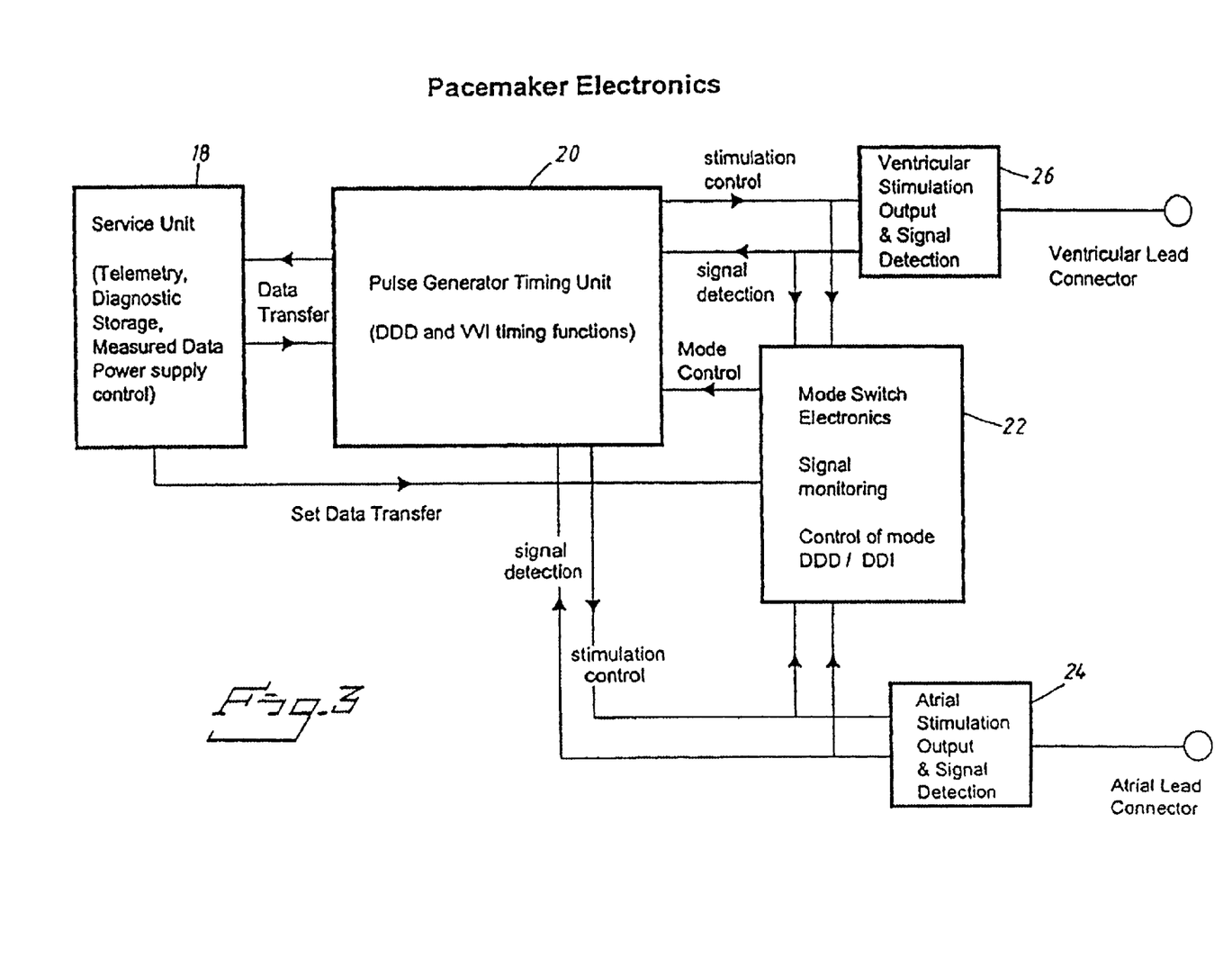
FIG. 3 shows the electronics of the pacemaker according to the invention in block form.

FIG. 3 shows in the form of a block diagram the electronics of the pacemaker 2 in FIG. 2. A service unit 18 includes electronics for test, control and communication (such as by telemetry), diagnostics, storage of measured data, power supply control etc. These components are not of primary importance for the invention and are well known to those skilled in the art and consequently need not be described in greater detail.

The pulse generator 20 is a timing unit, having DDD and DDI timing functions including electronics for control of time intervals and output of the pacemaker.

The mode switch electronics 22 includes a unit for signal monitoring and means for controlling the modes of operation. The different parts of this mode switch electronics 22 will be described more in detail below. Units 24 and 26, intended to be connected to the atrial lead and the ventricular lead, respectively, contain electronics for atrial stimulation output and ventricular stimulation output respectively, as well as signal detections. Thus these units 24, 26 include heart signal amplifiers and detectors, stimulation output stages, protection components and decoupling capacitors.

Figure 4:
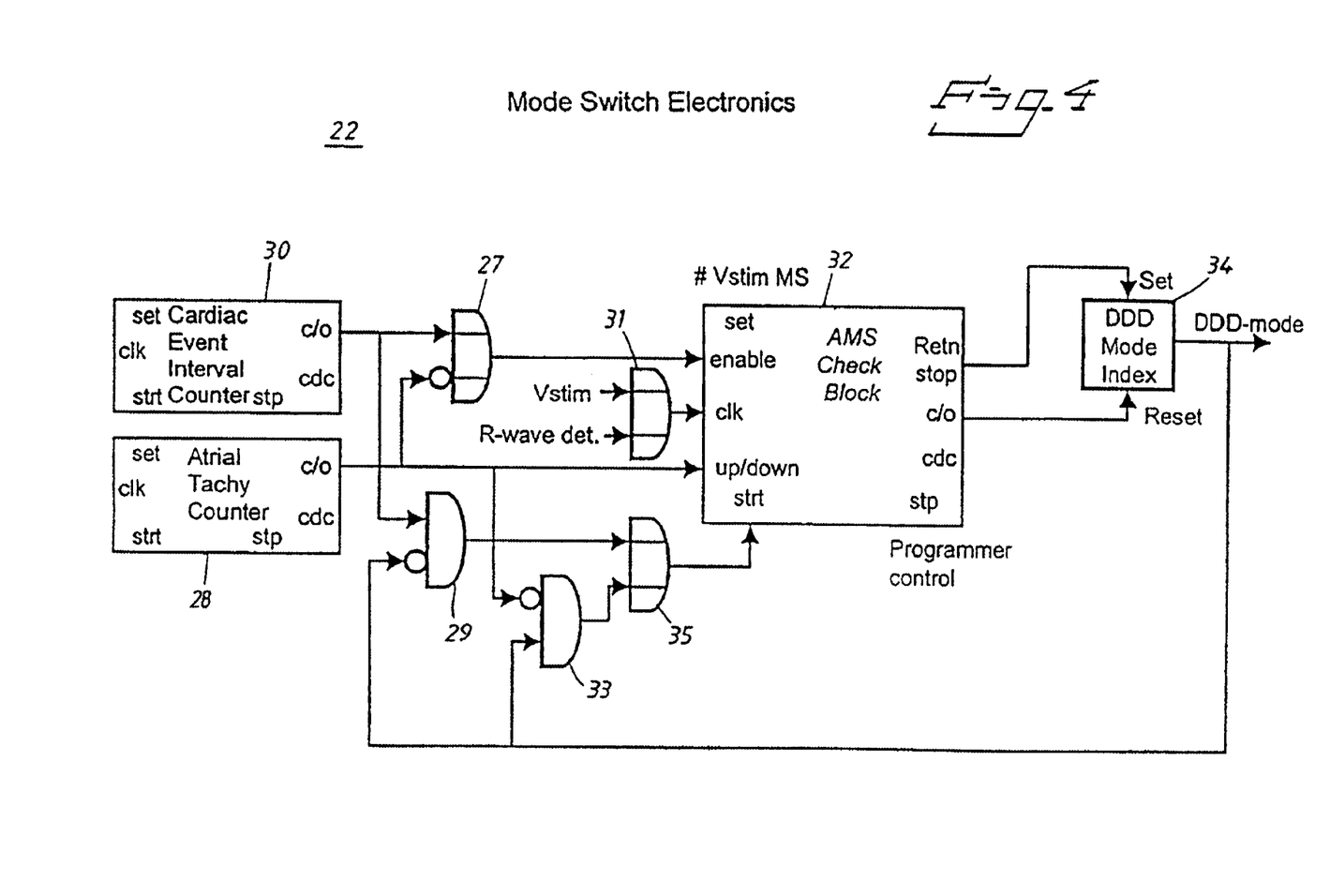
FIG. 4 illustrates the Mode Switch Electronics of the pacemaker according to the invention.

FIG. 4 shows the Mode Switch Electronics of block 22 in FIG. 3 in greater detail. This mode switch electronics 22 includes an Atrial Tachycardia Counter 28 and a Cardiac Event Interval Counter 30 in the form of two generalized counter blocks for checking intervals as will be described more in detail in the following.

An Automatic Mode Switch (AMS) Check Unit 32 contains electronics which are active during a check or consideration phase to determine whether a switch of the mode of operation of the pacemaker shall occur. The unit 32 includes a counter, described in greater detail with reference to FIGS. 10 and 11 in the following, which is arranged to count up or down depending on the incoming control signals.

A start signal is created a network of logic gates 27, 29, 31, 33 and 35 shown in FIG. 4. Thus in the DDD mode, when an atrial interval shorter than the tachycardia limit value is detected, a start signal will be generated. In a DDI mode, when one interval between any of two cardiac events, as measured by the Cardiac Event Interval Counter 30, is longer than the tachy limit value a start signal will also be generated.

An index register 34 is provided for storing the last decided mode during a new consideration phase, in which the automatic mode switch check unit 32 is active.

Figure 5:
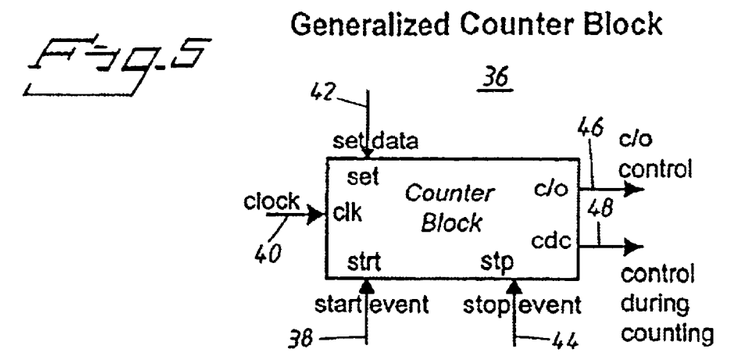
FIG. 5 shows a Generalized Counter Block for counting clock signals for time measurements in the pacemaker according to the invention.

FIG. 5 shows a generalized counter block 36 used as Atrial 5 Tachycardia Counter 28 and additional cardiac event interval counter 30 in FIG. 4. The current block 36 includes logic for control, counting of clock signals, and memorizing indications.

The function of the counter block 36 is as follows.

After receiving a start signal on the Start Event line 38, every clock pulse 40 is counted until the first of two possible events occurs. These events are the number of clock pulses 40 passes a specific pre-set value, set data 42, or a signal appears on the stop event line 44. The first of these two events to occur is indicated on the line c/o control 46. After a Start Event 38, during counting of the block 36, it is indicated on a Control During Counting line 48 that the counter block 36 is active.

The counter block 36 used as an Atrial Tachy Counter 28, see FIG. 4, is a time counter for determining the time between the detection of two consecutive atrial signals AF. The counter 28 starts and stops on detection of atrial signals or as a result of time out. Other cardiac events do not influence this counter 28. At an atrial signal AF detection the counter 28 is loaded with the predetermined tachy count limit ATI and the real time clock, 40 in FIG. 5, will decrement the counter 28. A new AF detection before the counter has reached zero results in a tachy indication. The occurrence of a time out, i.e. the counter 28 reaches zero, or an intervening ventricular stimulation V or ventricular signal detection R-wave results in a termination indication.

The counter block 36 in FIG. 5, used as Cardiac Event Interval Counter 30 in FIG. 4, is started and stopped on every cardiac event according to the following decision table.

| Denominations for the decision table | |
|---|---|
| A | Atrial stimulation |
| V | Ventricular stimulation |
| P | Atrial signal detection/P-wave detector |
| AF | Atrial signal detection |
| R | Ventricular signal detection/R-wave |
| VB | End of ventricular blanking period |
| ATI | Atrial Tachycardia Limit |
| UCP | UnCovering Process necessary to find eventually atrial signals during ventricular blanking |

| Decision Table of Tachycardia | | |
|---|---|---|
| Interval | Limit check | Decision |
| AF-AF* | <ATI | tachy |
| AF-AF | >ATI | non-tachy |
| AF-V | <ATI | terminated |
| AF-V | >ATI | non-tachy |
| AF-R | <ATI | terminated |
| AF-R | >ATI | non-tachy |

-continued

Decision Table of Tachycardia

| Interval | Limit check | Decision |
|---|---|---|
| AF-A | <ATI | terminated |
| AF-A | >ATI | non-tachy |
| VB-AF | <ATI | terminated, UCP |
| VB-AF | >ATI | non-tachy |
| VB-R | <ATI | terminated |
| VB-R | >ATI | non-tachy |
| VB-A | only >ATI | non-tachy |

Decision Table for the Mode Change Counter (MCC)
All indications are used during the period from one ventricular stimulation to the next ventricular stimulation.

| Indications | Counts |
|---|---|
| Tachy Indication & Dismissed Indications | MCC + 1 |
| Non-tachy Indication & Dismissed Indications | MCC – 1 |
| Only Dismissed Indications | MCC no change |
| Tachy Indication, then Non-Tachy Indication (and eventually Dismissed Indications) | MCC – 1 |
| Non-Tachy Indication, then Tachy Indication (and eventually Dismissed Indications) | MCC + 1 |

At the start the counter 30 is loaded with the predetermined Atrial Tachycardia Limit ATI and the real time clock 40, see FIGS. 4 and 5, will decrement the counter 30. Any stop of the counter 30 before it reaches zero will result in a termination indication and a time out of the counter 30 in a non-tachy indication as appears from the decision table above.

The Atrial Tachycardia Limit ATI, which is the interval limit value used in the pacemaker electronics, is programmable. The selected corresponding rate limit can thus be varied, preferably in steps of 10 beats per minute within the range 150–250 beats per minute.

Figure 6:
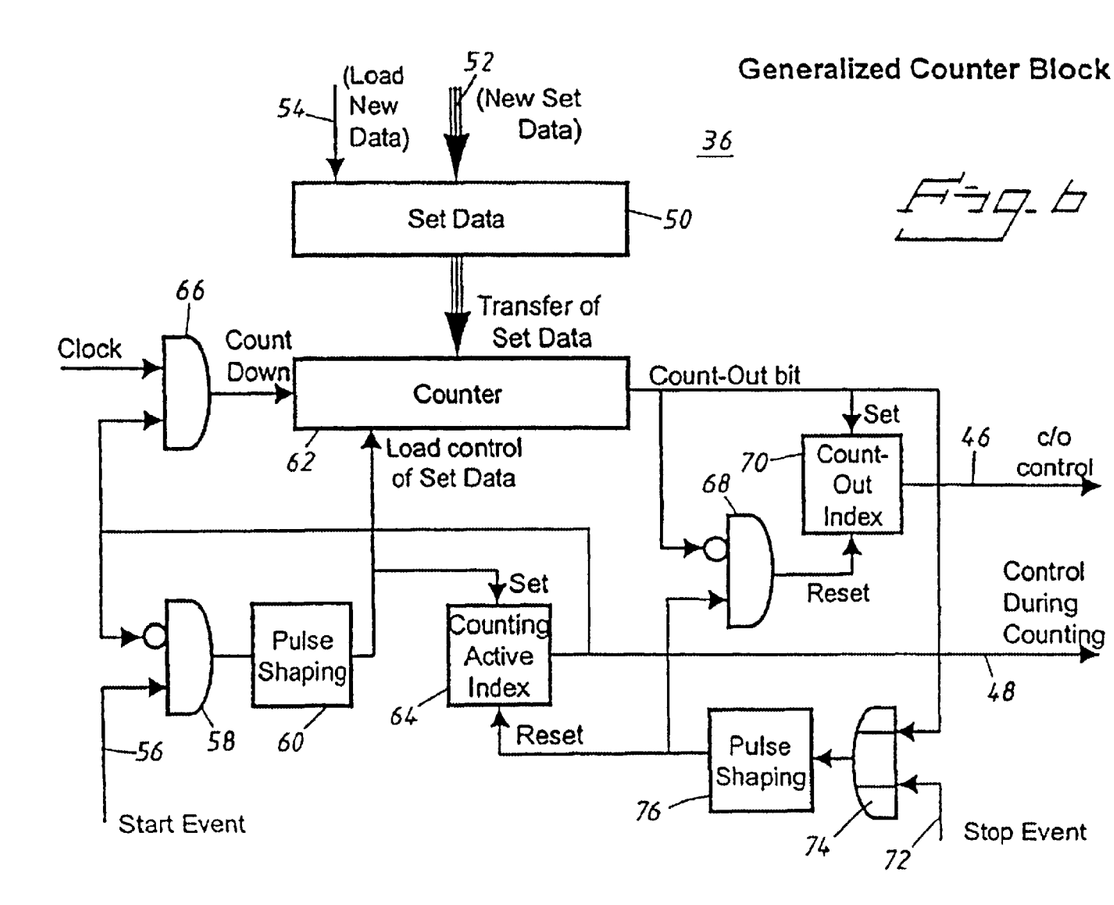
FIG. 6 illustrates more in detail the Generalized Counter Block shown in FIG. 5.

FIG. 6 is a block diagram of the Generalized Counter Block 36 shown in FIG. 5.

The counter block 36 controls other logic parts in the pacemaker through the two control lines do control 46, and Control During Counting 48. On the Control During Counting line 48 it is indicated that the counter is active, as mentioned before. On the c/o control line 46 it is indicated whether the counter has reached the same number of clock pulses 40 as the set binary value on line 42, cf. FIG. 5, or if the counting has been stopped by a stop event n line, 44 in FIG. 5, before counting out. These two possible occurrences result in opposite status on the c/o control 46.

The counter block 36 has a register 50 in which set data values are stored. These set data can be supplied from an external device through telemetry or can be produced internally in the pacemaker, cf. FIG. 3, and are normally kept constant. However, when new set data are stored these are supplied on data lines 52 and this supply is controlled by the load new data line 54.

The operation of the block shown in FIG. 6 is as follows. A Start Event control signal 56 is supplied through an AND-gate 58 having one of its inputs inverted to a unit 60 for reshaping the signal to a pulse suitable for processing in the counter block 62. A flip-flop Counting Active Index 64 is set to ON status by the reshaped start pulse delivered by the pulse shaping unit 60. This status information appears on the Control During Counting line 48. The reshaped start pulse delivered by the pulse shaping unit 60 also controls loading of binary data stored in the set data register 50 into the counter box 62.

When clock pulses are supplied through the AND-gate 66 to the counter 62 and the counting is active, the binary value in the counter 62 is counted down. When the count value zero is reached all binary bits in the counter 62 are equal to zero. On the next clock pulse all bits in the counter 62 will be changed to "one". There is one bit more in the counter 62 than the most significant bit in the value and when this extra bit changes from "zero" to "one", a Count-Out is indicated on the c/o control line 46. The most significant bit is always loaded from the set data register 50 as a "zero". At the Count-Out status the flip-flop Counting Active Index 64 is set to OFF status.

The gates shown in the block diagram in FIG. 6 control safe processing of the counter 62. Thus the AND-gate 66 which is connected to the clock input, insures that the counter 62 only counts down when the counter block is in its active stage.

The Start Event line 56 is connected to the pulse shaping unit 60 through an AND-gate 58 with one of its inputs inverted to protect loading of set data again after the counter has been active.

A similar AND-gate 68 with one of its inputs inverted is connected to a Count-Out Index 70 to prevent a Stop Event on line 72 through the OR-gate 74 and the pulse shaping unit 76 from changing this index after a Count-Out has occurred. The OR-gate 74 stops and resets the Counting Active Index 64 either as a result of a Stop Event on line 72 or a Count-Out event.

Figure 7:
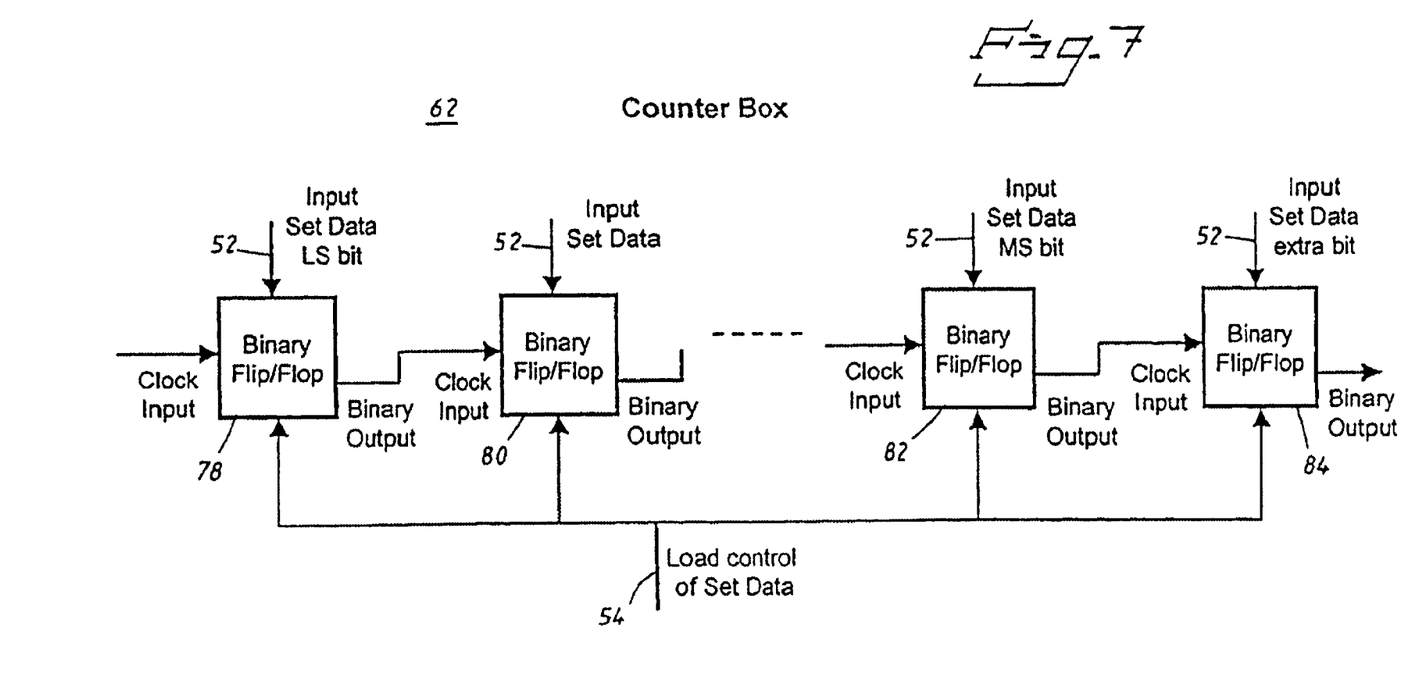
FIG. 7 shows the counter in FIG. 6 more in detail.

FIG. 7 shows the counter 62 in FIG. 6 in more detail. The counter 62 a sufficient number of binary stages 78, 80 . . . 82. In addition thereto there is an extra binary stage 84. Each binary stage 78, 80, 82, 84 can be loaded with one bit, "zero" or "one", from the set data register 50 in FIG. 6. This supply of set data is gated to occur when the load new data line 54, see FIG. 6, gets a pulse. The extra binary stage 84 will be loaded with the value "zero". When the counter 62 in FIG. 5 has counted down to the value "zero" on all stages 78, 80, . . . 82, 84, all stages 78, 80, . . . 82, 84 will switch to "one" in response to the next pulse. The signal from the last stage 84 controls the Count-Out indication and the deactivation of the counting.

Figure 8:
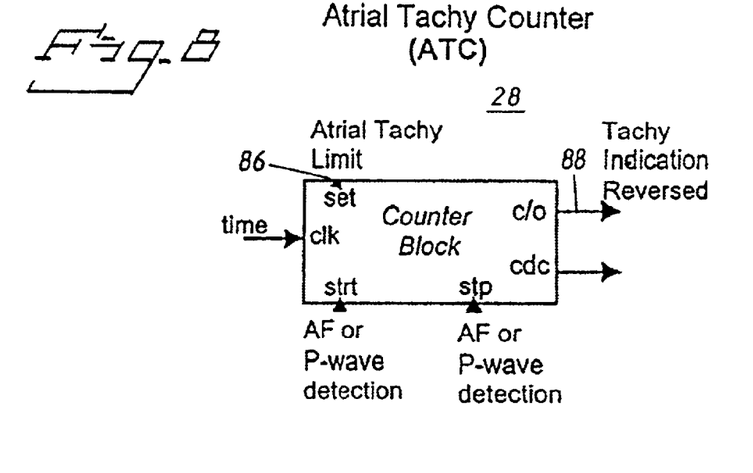
FIG. 8 shows the Atrial Interval Counter in the form of a Generalized Counter Block.

FIG. 8 shows the Atrial Tachy Counter (ATC) 28 of the Mode Switch Electronics shown in FIG. 4 in the form of a generalized counter block. This counter measures the time between two consecutive atrial events and compares this time with a predetermined Atrial Tachy Limit 86. An event can be any detection by the atrial P-wave detector or atrial tachycardia signal detector in the case when two separate atrial detectors are used. If there are other cardiac events during the counting procedure, e.g. a ventricular stimulation, these events do not influence this counter.

The set value of the counter 28 is the programmed Atrial Tachy Limit 86 for an atrial tachycardia.

In the example shown in FIG. 8 the output signal c/o on line 88 indicates that the last measured interval was not a tachy interval because there has been a Count-Out. This means that the signal on the co-line 88 is reversed. This is one essential element in the mode switch determination.

Figure 9:
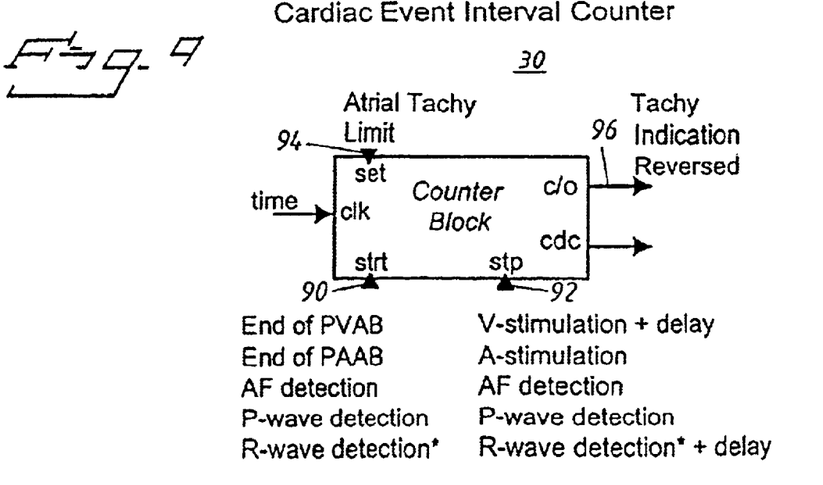
FIG. 9 shows a Cardiac Event Interval Counter in the form of a Generalized Counter Block.

FIG. 9 shows the Cardiac Event Interval Counter 30 in FIG. 3 in the form of a corresponding generalized counting block. With this counter 30 the time between the two latest cardiac events is measured and compared with the Atrial Tachy Limit.

Starting events 90 can be end of post ventricular atrial blanking (PVAB), which is a protection period in the detectors after a ventricular stimulation, and the end of post atrial—atrial blanking (PAAB), which is a protection period in the detectors after an atrial stimulation, an atrial tachycardia signal detection, P-wave detection or R-wave detection. R-wave detection can only be used if the so-called Combipolar mode of sensing is used, see below.

In a corresponding way stop events 92 can be a ventricular stimulation V-stimulation, an atrial stimulation, an atrial tachycardia signal detection, a P-wave detection or a R-wave detection, the last mentioned detection being possible only in case of Combipolar mode of sensing.

The set value 94 is also in this case the programmed Atrial Tachy Limit for an atrial tachycardia. In the example illustrated in the Figure an output c/o-signal on output 96 indicates that the measured interval was not a tachy interval, since there was a Count-Out. The non-tachy indication on the output 96 is one essential element in the mode switch determination.

Figure 10:
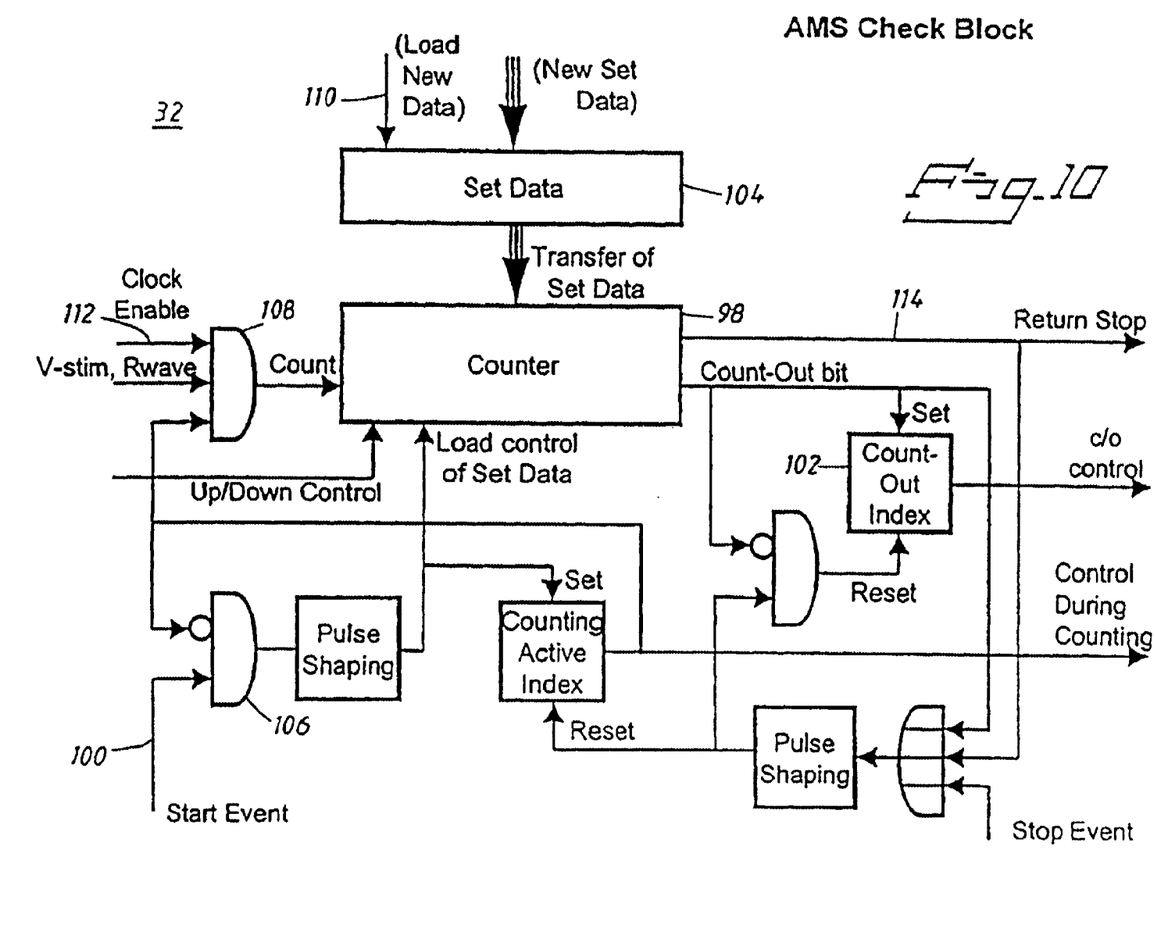
FIG. 10 shows more in detail the Automatic Mode Switch (AMS) Check Block of FIG. 4.

FIG. 10 is a block diagram the Automatic Mode Switch (AMS) Check Block 32 in FIG. 4. Most elements of the AMS Check Block are the same as those of the Generalized Counter Block 36, illustrated in FIG. 6. It is added the functions of counting up the counter 98 and comparison of the counter value with the set data value. Thus, after receipt of a start event on line 100, the Automatic Mode Switch Check Block 32 is activated until one of two possibilities occurs, viz. the counter reaches zero value or the set data value. Then the counter 98 is deactivated and a type of Count-Out is stored in the Count-Out Index Register 102.

The Set Data register 104 is in reality two different registers, each with its own Set Data value. One of these values is used when starting the counting in a DDD mode of operation and the other value when the counting is started in a DDI mode. Thus, when a start pulse is received the relevant value of these two values is loaded into the counter 98.

The AND-gate 106 with one of its inputs inverted prevents through the Load New Data line 108 loading of new Set Data after receipt of a start pulse.

The counter 98 is controlled by each detected ventricular event, i.e. a ventricular stimulation or an R-wave detection, supplied through the AND-gate 108. The counter 98 is controlled to count down if there is an indication that the measured interval in question in the Cardiac Event Interval Counter, see FIG. 9, is longer than the Atrial Tachy Limit. The counter 98 is controlled to count up if there is an indication that the measured interval between atrial signal detections is shorter than the Atrial Tachy Limit ATl. If none of these conditions is fulfilled the counting is terminated and the counter 98 disabled through the control line Clock Enable 112 to the AND-gate 108.

If the counter 98 reaches the same value as the set value and this occurs during counting up, a signal Return Stop is delivered by the counter 98 on its output 114. This signal Return Stop stops the activities in the Automatic Mode Switch Check Block and sets the Count-Out Index 102 to Count Out. This Count-Out Index 102 controls other parts of the pacemaker electronics to control the mode of operation. Thus, a Count-Out indication results in operation in the non-tracking mode (DDI) and an opposite indication or reversed Count-Out indication results in operation in the normal tracking mode (DDD).

Figure 11:
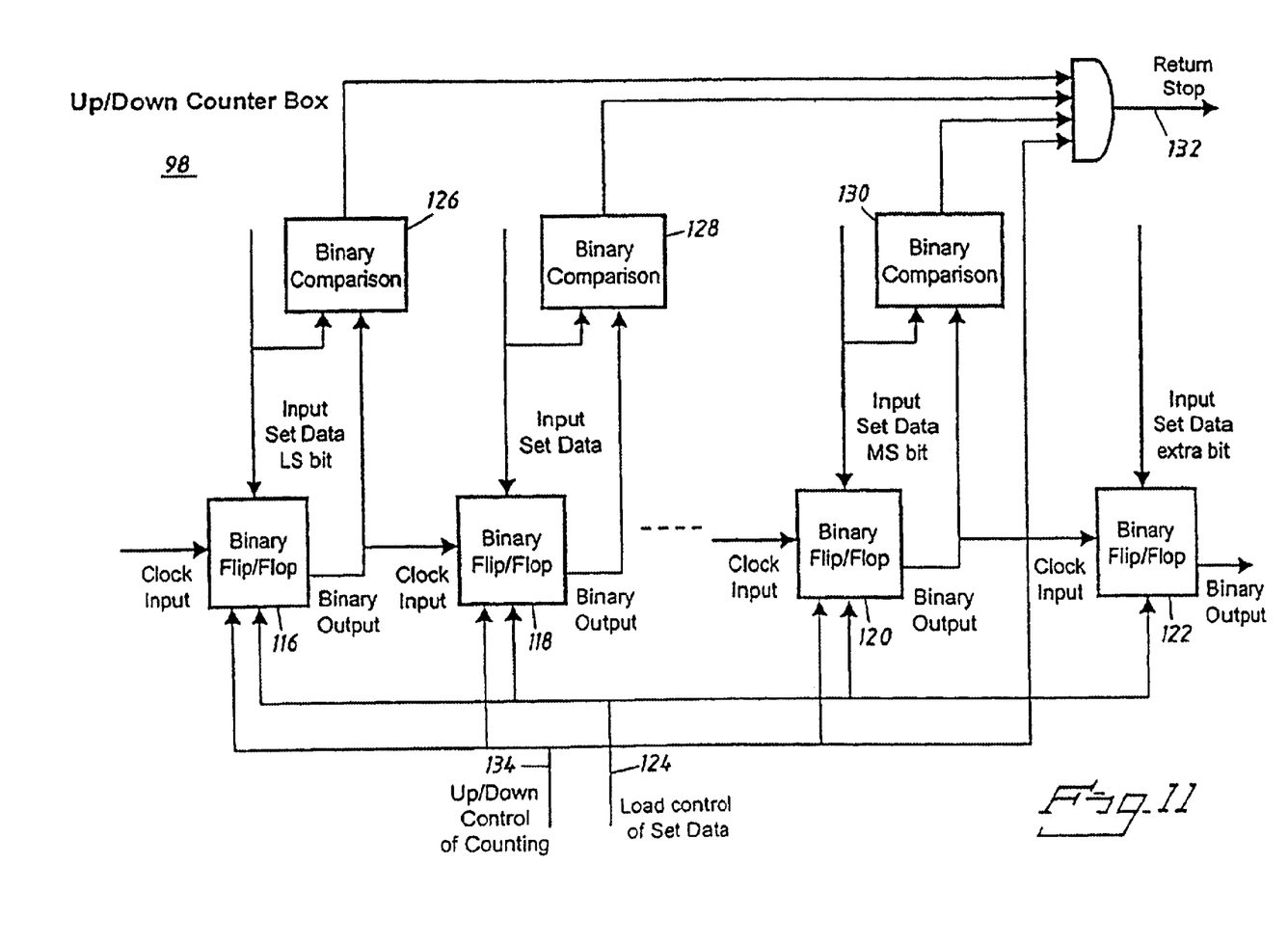
FIG. 11 shows more in detail the counter of the AMS Check Block shown in FIG. 10.

FIG. 11 shows the Up/Down Counter 98 more in detail. The counter 98 has a number of binary stages 116, 118 . . . 120 sufficient to be able to count the maximum desired value, plus one extra binary stage 122.

When the automatic mode switch procedure is started from the normal tracking mode (DDD), as indicated by an opposite or reversed Count-Out Index value, cf. the description of FIG. 10 above, a loading procedure is performed. Each binary stage 116, 118, . . . , 120 is then loaded with one bit, "zero"or "one", from the Set Data register, 104 in FIG. 10. This loading is gated to be performed when a pulse is received on the Load Control of Set Data line 124. The extra binary stage 122 will then be loaded with the binary value "zero". When the counter has counted down to "zero" on all stages 116, 118 . . . , 120, all stages 116, 118, . . . , 120 will be switched to "one" in response to the next pulse. The signal from the last stage 122 is controlling the Count-Out indication and the deactivation of the counting.

When the Automatic Mode Switch Check Block 32 in FIG. 10 is starting from the non-tracking mode (DDI), indicated by the Count-Out Index, no loading of the binary stages is performed since all bits are already set to "one". However, for the binary comparison in units 126, 128, 130, another value is used, which is equal to the number of ventricular intervals required for change from the DDI mode to the DDD mode. The selection of a suitable value for this binary comparison is performed in gates not shown in FIG. 11. In the units 126, 128, 130 a binary comparison is performed and when the counter value reaches the set value a Return Stop signal is delivered on the output 132. After start the counter is counting up or down depending on the logic state on the Up/Down Control of Counting line 134. The direction of the counting can be reversed after start of the counting.

A specific technique was described above using counters and decoding logics for counting a specific number of pulses. However, the essential function of the invention is to count a number of ventricular intervals during a check of tachycardia indications for deciding whether to make a mode switch, and the same or similar functions can also be realized by using other techniques, e.g. microprocessor techniques.

In summary, in the pacemaker according to the invention a mode switch from a tracking mode of operation, e.g. DDD, to a nontracking mode, e.g. DDI, is performed when there is an atrial tachycardia with a rate exceeding a programmed limit. The determination and confirmation that a state of atrial tachycardia actually prevails are performed by using a predetermined number of stimulation intervals during which other, or preferably all, cardiac signal intervals are analyzed. This phase after detection of an atrial tachycardia in DDD mode or detection of a disappeared tachycardia in DDI mode is called consideration or check phase, during which it is considered or checked if the mode should be switched or not.

Atrial events are continuously monitored by an atrial tachycardia signal detector or P-wave detector and when the interval between two consecutive atrial signals is less than a programmed atrial tachycardia limit value an index memory is set to tachy indication. When there is a measured interval between any cardiac event during a subsequent cardiac cycle, which is longer than the programmed tachycardia limit value, the index memory is set to a non-tachy indication. The interval measurements are accomplished by two interval counters, viz. an Atrial Tachy Counter and a Cardiac Event Interval Counter. The measured values are compared to the programmed tachycardia limit value and the result of the comparison is stored in ON/OFF memories. The index information is used at the next ventricular stimulation to increase the safety in the determination of whether a state of tachycardia prevails, before the final decision of pacemaker mode of operation is made. Thus, at each ventricular stimulation the previous indication in the index memory is used to count up or count down the mode change counter. If there was at least one indication du ring the interval between two consecutive ventricular stimulations, the mode change counter is decremented by one if the last indication is a tachy, and, if the last indication is non-tachy, the counter is counted down by one. If there is no new indication during the interval between two consecutive ventricular stimulations the mode change counter is not altered. When the counted value reaches a programmed limit a mode switch occurs on the next ventricular stimulation.

A spontaneous ventricular beat, R-wave, controls the mode change counter in the same way as a ventricular stimulation.

After a mode change to a non-tracking or non-synchronous mode, for example DDI or VVI, the ventricle is stimulated with a basic rate during the state of atrial tachycardia. This basic rate can be constant, for instance with a somewhat higher value than the basic rate used in the tracking DDD-mode of operation. The basic rate can, however, be varied under the control of one or more activity or physiological sensors.

Thus, the pacemaker according to the invention operates as follows.

The atrial signals are continuously monitored, including after a mode change. As long as the indication in the index memory then shows an ongoing tachycardia the non-tracking or non-synchronous mode of operation is maintained. If a non-tachy indication appears the mode change counter will count correspondingly on the issue of the next ventricular stimulation or R-wave detection. After the mode change counter has counted down to the programmed limit number, the mode of operation is changed back to DDD.

At detection of a tachycardia the number of high rate synchronized stimulation intervals is limited to a programmed number, e.g. 3 and thereafter the mode will change to a non-synchronized mode like DDI. The similar principle is used for changing back to the synchronous DDD mode after disappearance of the atrial tachycardia. The number of stimulation intervals at the base rate without a tachycardia is programmable.

The atrial tachycardia limit value is stored in the pacemaker. This limit value can suitably be a value in the range 400 ms–240 ms, corresponding to 150–250 beats per minute. Every measured atrial interval shorter than the atrial tachycardia limit ATI and longer than a value of e.g. 140 ms is then indicated as a tachy interval. The atrial tachycardia rate can suitably be varied in steps of 10 beats per minute.

For the detectors a Combipolar configuration can be used, as indicated above, or the normal bipolar configuration. The Combipolar technique is described in e.g. Herzschrittmacher 17:2, 1997, p.108 and European Application 0 596 319. As the Combipolar lead configuration gives AV-differential signals, it is important that the logic conclusions are appropriately designed to avoid that ventricular signals are falsely interpreted as atrial signals.

A situation in which the measured interval between two atrial signals is longer than the atrial tachy limit and no other interval is longer than the atrial tachy limit, this could indicate that there is a covered atrial signal during the ventricular blanking period. For the atrial tachycardia signal detection no refractory period is used, only a technical blanking period to avoid crosstalk sensing in Combipolar mode of sensing at a ventricular stimulation or at the appearance of an R-wave. In some tachycardia situations stable covering of atrial tachycardia signals may thus occur by the blanking interval following the ventricular stimulation. The basic criterion for uncovering thus is a change during one or more stimulation intervals of the time for the ventricular stimulation. This change of time can be obtained by temporary changes of one of the pacemaker parameters resulting in a shortening or a prolonging of the PV-intervals. A suitable uncovering method for this purpose is described in U.S. Pat. No. 5,683,428.

As mentioned above two types of atrial signals should be detected, viz. normal P-waves and atrial signals at atrial tachycardia. Normal P-waves for controlling the pacemaker stimulation rhythm have a stable amplitude with a variation normally less than ±15%. A detector sensitivity that is too high can give rise to interference detections, which is not acceptable since such false detections will influence the rhythm of the normal pacemaker operation. In the case of an atrial tachycardia or an incipient atrial tachycardia the amplitude of the atrial signals normally decreases, although they sometimes increase. Atrial fibrillation signals have, however, low and varying amplitudes and also a bad slew rate compared to normal P-waves and therefore a higher atrial detection sensitivity is needed for detection of these signals.

The preferred way of detecting the atrial signals is therefore to use one atrial signal detector for normal P-waves and one detector adapted for detecting atrial signals of lower amplitudes. The ratio between the sensitivities of the detector for detecting atrial signals in case of an incipient tachycardia and the sensitivity of the normal P-wave detector can preferably be changed in steps of 0.4 in the range 1.2–2.0. For these two detectors two separate amplifier and filter paths adapted to the signals in question, are provided in the pacemaker electronics. The filters must be designed for adequate R-wave attenuation and T-wave attenuation. Also myocardial signals have to be attenuated and the filters must be designed to avoid ringing on the signals.

Instead of two separate detectors it is, however, possible to use the ordinary P-wave detector, and then with two separate tachy sensitivity settings, one sensitivity suitable for the atrial signal detection at atrial tachycardia and one suitable for ordinary P-wave detection.

The above described embodiments of the pacemaker according to the invention are dual chamber pacers. However, the invention can be applied to left ventricle pacing or four chamber pacers as well.

Although modifications and changes may be suggested by those skilled in the art, it is the intention of the inventor to embody within the patent warranted hereon all changes and modifications as reasonably and properly come within the scope of his contribution to the art.

I claim:

1. A pacemaker comprising:
    an atrial detector adapted for interaction with a subject to detect atrial events;
    a ventricular detector adapted for interaction with said subject to detect ventricular events;
    an atrial interval determination unit for determining an interval between successive atrial events detected by said atrial detector;
    a comparator for comparing said interval with a predetermined atrial tachycardia limit value and which generates and records an indication of atrial tachycardia if said interval is less than said atrial tachycardia limit value;

a stimulation administration arrangement adapted for interaction with said subject to administer stimulating therapy to said subject in a tracking mode and in a non-tracking mode;

a mode switching unit connected to said comparator and to said stimulation administration arrangement for switching said stimulation administration arrangement from said tracking mode to said non-tracking mode when a number of said indications of atrial tachycardia recorded by said comparator reaches a predetermined count limit;

a cardiac event interval determination unit for determining additional intervals between cardiac events detected by said atrial detector or said ventricular detector, during a pacemaker interval selected from the group consisting of an interval between two consecutive ventricular stimulations by said stimulation administration arrangement and two consecutive R-wave detections by said ventricular detector; and said cardiac event interval determination unit supplying said additional intervals to said comparator, and said comparator comparing said additional intervals to said tachycardia limit value and generating a non-tachycardia indication which reduces the recorded number of said indications of atrial tachycardia by one if at least one of said additional intervals during said pacemaker interval is longer than said tachycardia limit value.

2. A pacemaker as claimed in claim 1 wherein said cardiac event interval determination unit determines all intervals during said pacemaker interval detected by said atrial detector and said ventricular detector.

3. A pacemaker as claimed in claim 1 wherein said atrial detector comprises a P-wave detector for detecting normal sinus P-waves with a first sensitivity, and an atrial tachycardia detector for monitoring signals representative of atrial tachycardia, with a second sensitivity that is higher than said first sensitivity.

4. A pacemaker as claimed in claim 1 wherein said mode switching unit comprises an up/down counter which is incremented by one upon each indication of tachycardia and which is decremented by one by each non-tachycardia indication.

5. A pacemaker as claimed in claim 4 wherein said mode switching unit switches said stimulation administration arrangement back to said tracking mode if said up/down counter is decremented by a predetermined number from a count representing said tachycardia limit value.

6. A pacemaker as claimed in claim 4 wherein said mode switching unit switches said stimulation administration arrangement back to said tracking mode if said up/down counter is decremented to zero.

7. A pacemaker as claimed in claim 1 wherein said cardiac interval determining unit comprises at least one counter that is started by a detected cardiac event to count clock pulses until a preset value is reached corresponding to said tachycardia limit value, or until a stop event is detected by one of said atrial detector and said ventricular detector.

8. A pacemaker as claimed in claim 1 wherein said non-tracking mode is a DDI mode.

9. A pacemaker as claimed in claim 1 further comprising a unit for modifying an AV interval to allow detection of atrial events occurring within a ventricular blanking period.

10. A pacemaker as claimed in claim 9 wherein said unit for modifying the AV interval shortens said AV interval in response to a decrease of said pacemaker interval below a predetermined limit.

11. A pacemaker as claimed in claim 10 wherein said predetermined limit is twice said atrial tachycardia limit value.

12. A pacemaker as claimed in claim 1 wherein said stimulation administration arrangement generates stimulation pulses at a stimulation rate equal to a base rate upon detection of decreased cardiac activity by at least one of said atrial detector and said ventricular detector.

13. A pacemaker as claimed in claim 12 further comprising a sensor which detects a signal related to cardiac activity, said sensor being connected to said stimulation administration arrangement for setting said base rate dependent on said signal from said sensor.

* * * * *